US007215993B2

(12) United States Patent
Lin

(10) Patent No.: US 7,215,993 B2
(45) Date of Patent: May 8, 2007

(54) CARDIAC RHYTHM MANAGEMENT SYSTEMS AND METHODS FOR DETECTING OR VALIDATING CARDIAC BEATS IN THE PRESENCE OF NOISE

(75) Inventor: Yayun Lin, St. Paul, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 560 days.

(21) Appl. No.: 10/213,364

(22) Filed: Aug. 6, 2002

(65) Prior Publication Data

US 2004/0030256 A1 Feb. 12, 2004

(51) Int. Cl.
*A61B 5/0456* (2006.01)
(52) U.S. Cl. .............. 600/521; 500/509; 500/515
(58) Field of Classification Search ........ 600/515, 600/517, 521, 508, 509; 607/9, 27, 28; 128/901
See application file for complete search history.

(56) References Cited

U.S. PATENT DOCUMENTS

| | | | |
|---|---|---|---|
| 4,432,362 A | 2/1984 | Leckrone et al. | ..... 128/419 PG |
| 4,589,420 A | 5/1986 | Adams et al. | |
| 4,679,144 A | 7/1987 | Cox et al. | |
| 4,779,617 A | 10/1988 | Whigham | ..... 128/419 P |
| 4,913,146 A | 4/1990 | DeCote, Jr. | ..... 128/419 |
| 4,960,123 A | 10/1990 | Maker | ..... 128/419 D |
| 5,010,887 A | 4/1991 | Thornander | ..... 128/696 |
| 5,188,117 A | 2/1993 | Steinhaus et al. | ..... 128/708 |
| 5,209,237 A | 5/1993 | Rosenthal | ..... 128/698 |
| 5,370,124 A * | 12/1994 | Dissing et al. | ..... 600/508 |
| 5,492,128 A | 2/1996 | Wickham | ..... 128/696 |

(Continued)

FOREIGN PATENT DOCUMENTS

WO  WO-01/43820  6/2001

(Continued)

OTHER PUBLICATIONS

Definition of "statistic" from The American Heritage Dictionary, Second College Edition (1982).*

(Continued)

*Primary Examiner*—George Manuel
*Assistant Examiner*—Nicole R. Kramer
(74) *Attorney, Agent, or Firm*—Schwegman, Lundberg, Woessner, & Kluth

(57) ABSTRACT

This document describes systems, devices, and methods for detecting or validating cardiac beats, such as in the presence of myopotential or other noise. In one example, an amplitude peak, which is a candidate for a detected cardiac beat, is used in a weighted average, along with a preceding and subsequent sample. The weighted average is compared to a noise threshold. Based on the result of comparison, the amplitude peak is either deemed an actual cardiac beat, or otherwise is deemed noise. The described systems, devices, and methods improve the accuracy of detecting an actual cardiac beat in the presence of noise, during normal sinus rhythm or during an arrhythmia such as ventricular fibrillation. This, in turn, improves the accuracy with which therapy is delivered or withheld by an implantable cardiac rhythm management device. In one example, such as where the system includes a cardiac signal detector with automatic gain control (AGC) circuitry, the weighted average is normalized.

35 Claims, 7 Drawing Sheets

U.S. PATENT DOCUMENTS

| | | | |
|---|---|---|---|
| 5,522,857 A | 6/1996 | van Krieken | 607/9 |
| 5,562,713 A | 10/1996 | Silvian | 607/32 |
| 5,564,430 A | 10/1996 | Jacobson et al. | 128/697 |
| 5,573,550 A | 11/1996 | Zadeh et al. | 607/28 |
| 5,591,214 A | 1/1997 | Lu | 607/9 |
| 5,613,495 A | 3/1997 | Mills et al. | 128/686 |
| 5,647,379 A | 7/1997 | Meltzer | 128/891 |
| 5,697,958 A | 12/1997 | Paul et al. | 607/31 |
| 5,702,425 A | 12/1997 | Wickham | 607/9 |
| 5,702,427 A | 12/1997 | Ecker et al. | 607/28 |
| 5,709,215 A | 1/1998 | Perttu et al. | 128/708 |
| 5,755,738 A | 5/1998 | Kim et al. | 607/9 |
| 5,766,227 A | 6/1998 | Nappholz et al. | 607/9 |
| 5,778,881 A | 7/1998 | Sun et al. | 128/696 |
| 5,782,876 A | 7/1998 | Flammang | 607/4 |
| 5,792,212 A | 8/1998 | Weijand | 607/73 |
| 5,817,130 A | 10/1998 | Cox et al. | 607/5 |
| 5,817,135 A | 10/1998 | Cooper et al. | 607/17 |
| 5,861,008 A | 1/1999 | Obel et al. | 607/11 |
| 5,865,749 A | 2/1999 | Doten et al. | 600/443 |
| 5,867,361 A | 2/1999 | Wolf et al. | 361/302 |
| 5,870,272 A | 2/1999 | Seifried et al. | 361/302 |
| 5,871,509 A | 2/1999 | Noren | 607/9 |
| 5,891,171 A | 4/1999 | Wickham | 607/4 |
| 5,897,575 A | 4/1999 | Wickham | 607/4 |
| 5,957,857 A | 9/1999 | Hartley | 600/521 |
| 5,978,710 A | 11/1999 | Prutchi et al. | 607/17 |
| 5,999,848 A | 12/1999 | Gord et al. | 607/2 |
| 6,029,086 A | 2/2000 | Kim et al. | 607/9 |
| 6,031,710 A | 2/2000 | Wolf et al. | 361/302 |
| 6,063,034 A | 5/2000 | Doten et al. | 600/448 |
| 6,068,589 A | 5/2000 | Neukermans | 600/25 |
| 6,070,097 A | 5/2000 | Kreger et al. | 600/521 |
| 6,097,983 A * | 8/2000 | Strandberg | 607/9 |
| 6,112,119 A | 8/2000 | Schuelke et al. | 607/9 |
| 6,195,585 B1 | 2/2001 | Karunasiri et al. | 607/57 |
| 6,198,968 B1 | 3/2001 | Prutchi et al. | 607/9 |
| 6,201,993 B1 | 3/2001 | Kruse et al. | 607/30 |
| 6,208,900 B1 | 3/2001 | Ecker et al. | 607/17 |
| 6,223,083 B1 | 4/2001 | Rosar | 607/60 |
| 6,230,059 B1 | 5/2001 | Duffin | 607/60 |
| 6,236,882 B1 | 5/2001 | Lee et al. | 600/509 |
| 6,272,381 B1 | 8/2001 | Callaghan et al. | 607/26 |
| 6,282,446 B1 | 8/2001 | Eberle et al. | 607/5 |
| 6,321,115 B1 | 11/2001 | Mouchawar et al. | 607/9 |
| 6,421,554 B1 | 7/2002 | Lee et al. | |
| 6,505,071 B1 | 1/2003 | Zhu et al. | |
| 6,892,092 B2 | 5/2005 | Palreddy et al. | |
| 6,917,830 B2 | 7/2005 | Palreddy et al. | |
| 2003/0083713 A1 | 5/2003 | Palreddy et al. | 607/28 |
| 2004/0106957 A1 | 6/2004 | Palreddy et al. | |
| 2005/0192504 A1 | 9/2005 | Palreddy et al. | |

FOREIGN PATENT DOCUMENTS

WO    WO-2005/018738 A1    3/2005

OTHER PUBLICATIONS

Gunderson, Bruce., "Automatic Identification of ICD Lead Problemms Using Electrograms", *Pace*, vol. 24, p. 664, Apr. 2002, (2002),664.

* cited by examiner

CARDIAC RHYTHM MANAGEMENT SYSTEMS AND METHODS FOR DETECTING OR VALIDATING CARDIAC BEATS IN THE PRESENCE OF NOISE

TECHNICAL FIELD

This document relates generally to medical systems, devices, and methods, and particularly, but not by way of limitation, to cardiac rhythm management systems and methods for detecting and/or validating cardiac beats, even in the presence of noise.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (i.e., a "surface ECG signal") obtained from electrodes placed on the patient's skin, or from electrodes implanted within the patient's body (i.e., an "electrogram signal"). The surface ECG and electrogram waveforms, for example, include artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poor spatial coordination of heart contractions. In either case, diminished blood circulation may result. For such patients, a cardiac rhythm management system may be used to improve the rhythm and/or spatial coordination of heart contractions. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart.

One problem faced by cardiac rhythm management devices is in detecting the atrial and/or ventricular depolarizations in the intrinsic electrical cardiac signals, since the delivery of therapy to the heart is typically based at least in part on the timing and/or morphology of such detected depolarizations. To detect a depolarization event, the cardiac signal may be amplified, filtered, and/or level-detected (e.g., to determine whether an artifact exceeds a particular threshold level associated with an atrial or ventricular depolarization). Depolarization detection is complicated, however, by the fact that the intrinsic cardiac signals may include noise unrelated to the heart depolarization. The noise may arise from a variety of sources, including, among other things: myopotentials associated with skeletal muscle contractions; a loose or fractured leadwire providing intermittent contact between the device and the heart; or, electromagnetic interference from AC power provided to nearby electrical equipment (e.g., 60 Hertz), from nearby switching power supplies, from a nearby electrosurgical tool, from communication equipment, or from electronic surveillance equipment. Noise erroneously detected as a heart depolarization may inappropriately inhibit bradyarrhythmia pacing therapy or cardiac resynchronization therapy, or may inappropriately trigger tachyarrhythmia shock therapy. For these and other reasons, the present inventor has recognized a need for improved techniques for discriminating between a depolarization, which is associated with a cardiac beat, and noise, which is not.

SUMMARY

This document discusses, among other things, systems devices and methods for detecting or validating cardiac beats in the presence of noise.

In a first example, this document discusses a system includes a cardiac signal detector. The cardiac signal detector includes a detector input configured to be coupled to a first electrode associated with a heart. The cardiac signal detector also includes a detector output providing a sampled cardiac signal. The system also includes a signal processor circuit, coupled to the detector output. The signal processor circuit is configured to distinguish, using a peak sample, a preceding sample to the peak sample, and a subsequent sample to the peak sample, a cardiac depolarization from noise.

In one variation, the signal processor circuit is configured to compute a statistic using the peak sample, the preceding sample, and the subsequent sample, and to distinguish between a cardiac depolarization and noise by comparing the statistic to a predetermined threshold value. In another variation, the signal processor circuit is configured to compute a weighted average using the peak sample, the preceding sample, and the subsequent sample, and to distinguish between a cardiac depolarization and noise by comparing the weighted average to a predetermined threshold value. In a further variation, the signal processor circuit is configured to compute a normalized weighted average using the peak sample, the preceding sample, and the subsequent sample, and to distinguish between a cardiac depolarization and noise by comparing the normalized weighted average to a predetermined threshold value. In another variation, the normalized weighted average is computed as NWA=[P(n−1)+2*P(n)+P(n+1)]/[4*P(n)]. In another variation, the predetermined threshold value is about 0.62. In a further variation, the system also includes an electrode. In another variation, the system includes an intracardiac leadwire carrying the electrode. In a further variation, the system also includes an implantable device including the cardiac signal detector and the signal processing circuit, and a remote user interface, configured to be communicatively coupled to the implantable device.

In a second example, this document discusses an implantable cardiac rhythm management device. The device includes a cardiac signal detector. The cardiac signal detector includes a cardiac signal detector input configured to be coupled to a first electrode associated with a heart to receive an intrinsic cardiac signal therefrom. The cardiac signal detector also includes a cardiac signal detector output providing a sampled cardiac signal. The device also includes a depolarization detector circuit, coupled to the first electrode. The depolarization detector circuit includes a level detector circuit configured to detect an intrinsic heart depolarization on the intrinsic cardiac signal. The device also includes a signal processor circuit. The signal processor circuit is coupled to the cardiac signal detector output and the depolarization detector circuit. The signal processor circuit is configured to validate the intrinsic heart depolarization detected by the depolarization detector circuit by distinguishing a cardiac depolarization from noise, using a peak sample of the sampled cardiac signal, a preceding sample to the peak sample of the sampled cardiac signal, and a subsequent sample to the peak sample of the sampled cardiac signal. The peak sample of the sampled cardiac signal is associated with a peak of the intrinsic heart depolarization detected by the depolarization detector circuit.

In one variation, the signal processor circuit is configured to compute a weighted average using the peak sample, the preceding sample, and the subsequent sample, and to distinguish between a cardiac depolarization and noise by comparing the weighted average to a predetermined threshold value. In another variation, the weighted average is computed as NWA=[P(n−1)+2*P(n)+P(n+1)]/[4*P(n)].

In a third example, this document discusses a method. The method includes sampling a cardiac signal. A peak sample is detected from the cardiac signal. A preceding sample to the peak sample is detected from the cardiac signal. A subsequent sample to the peak sample is detected from the cardiac signal. The method includes distinguishing, using the peak sample, the preceding sample, and the subsequent sample, a cardiac depolarization from noise.

In one variation, the distinguishing includes computing a statistic using the peak sample, the preceding sample, and the subsequent sample. The distinguishing between a cardiac depolarization and noise includes comparing the statistic to a predetermined threshold value. In a further variation, the computing includes computing a weighted average using the peak sample, the preceding sample, and the subsequent sample, and distinguishing between a cardiac depolarization and noise by comparing the weighted average to a predetermined threshold value. In another variation, the computing includes computing a normalized weighted average using the peak sample, the preceding sample, and the subsequent sample, and distinguishing between a cardiac depolarization and noise by comparing the normalized weighted average to a predetermined threshold value. In a further variation, the normalized weighted average is computed as NWA=[P(n−1)+2*P(n)+P(n+1)]/[4*P(n)]. In another variation, the comparing the normalized weighted average to the predetermined threshold value comprises using a predetermined threshold value of about 0.62. A further variation includes programming the predetermined threshold value. Yet another variation includes detecting the cardiac signal using an electrode. Another variation includes intravascularly disposing the electrode within the heart. A further variation includes communicating an indication of whether a peak sample is a depolarization or noise to a remote location.

In a fourth example, this document discusses a method. The method includes detecting an intrinsic cardiac signal, detecting a depolarization on the intrinsic cardiac signal by comparing a level of the intrinsic cardiac signal to a level threshold value to yield a level-detected depolarization, sampling the intrinsic cardiac signal to produce a sampled cardiac signal, detecting a peak sample from the sampled cardiac signal, wherein the peak sample is associated with the level-detected depolarization, detecting a preceding sample to the peak sample from the sampled cardiac signal, detecting a subsequent sample to the peak sample from the sampled cardiac signal, and validating, using the peak sample, the preceding sample, and the subsequent sample, the level-detected depolarization by computing a weighted average using the peak sample, the preceding sample, and the subsequent sample, and comparing the weighted average to a noise threshold. In one variation, the computing the weighted average is computed as NWA=[P(n−1)+2*P(n)+P(n+1)]/[4*P(n)].

This document also includes experimental data that illustrates the detecting/validating during normal sinus rhythm, as well as during an arrhythmia, such as the onset of ventricular fibrillation. Other aspects of the present systems, devices, and methods will become apparent upon reading the following detailed description and viewing the drawings that form a part thereof.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

This document discusses, among other things, systems, devices, and methods that will be described in applications involving implantable medical devices including, but not limited to, implantable cardiac rhythm management systems such as pacemakers, cardioverter/defibrillators, pacer/defibrillators, biventricular or other multi-site resynchronization or coordination devices, and drug delivery systems. However, these systems, devices, and methods may be employed in unimplanted devices, including, but not limited to, external pacemakers, cardioverter/defibrillators, pacer/defibrillators, biventricular or other multi-site resynchronization or coordination devices, monitors, programmers and recorders, whether such devices are used for providing a diagnostic, a therapy, or both a diagnostic and a therapy.

Figure 1:
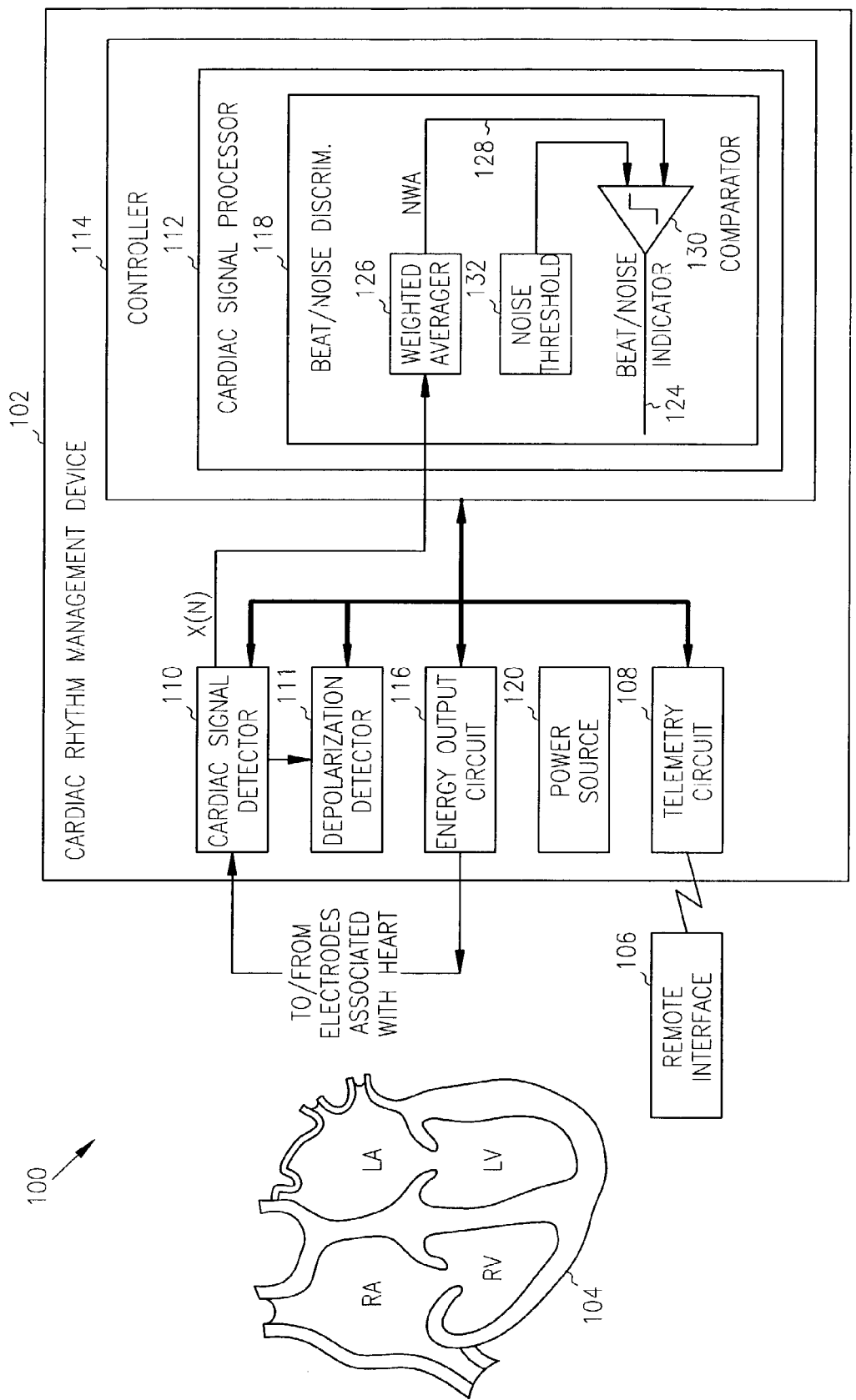
FIG. 1 is a schematic diagram illustrating generally, by way of example, but not by way of limitation, portions of a cardiac rhythm management system.

FIG. 1 is a block diagram illustrating generally portions of a cardiac rhythm management system 100 and portions of an environment in which it is used. In this example, system 100 includes a cardiac rhythm management device 102 coupled to a heart 104 by one or more electrodes associated with heart 104, such as for sensing intrinsic cardiac signals and/or for delivering energy or other therapy to heart 104. System 100 also includes a programmer or other remote interface 106, which is wirelessly or otherwise communicatively coupled to a telemetry circuit 108 or other communication circuit in device 102. Device 102 includes a pacer, a defibrillator, a cardiac resynchronization therapy (CRT) device, a monitor, a device that combines more than one of these functions, or any other implantable or external device for diagnosing and/or treating the heart. In one example, device 102 is sized and shaped for being pectorally or abdominally implanted in a human patient. The electrode(s) coupling device 102 to heart 104 may include an intravascular electrode, an intracardiac electrode, an epicardial electrode, or a housing or a header electrode located on a housing of device 102 or a header attached thereto, or any combination of the above. In some configurations, such as where portion(s) of device 102 are external to the patient, the electrode(s) coupling device 102 to heart 104 may include a skin surface electrode external to the patient. The electrodes may be associated with the heart for bipolar (i.e., two electrodes that are relatively close together) or for unipolar (i.e., two electrodes that are farther apart) signal sensing or therapy energy delivery (e.g., pacing pulse or shocks). In one example, the electrodes include a tip electrode located at or near a right ventricular apex of heart 104 and a shock or coil electrode located slightly superior thereto within the right ventricle of heart 104.

In the example of FIG. 1, device 102 includes a cardiac signal detector 110 having an input coupled to heart 104 by electrodes associated with heart 104 in a suitable manner for sensing an intrinsic cardiac signal. Detector 110 need not actually extract heart depolarizations from the sensed intrinsic cardiac signal; such functions may be performed elsewhere in device 102, such as by depolarization detector 111. Detector 110 typically includes a sense amplifier for acquiring and amplifying the cardiac signal. Detector 110 may also include one or more continuous-time and/or discrete time (e.g., switched-capacitor) filter circuits, such as for selectively emphasizing the desired heart depolarization information relative to other acquired signal content. Detector 110 may also include an analog-to-digital converter (ADC) to convert continuous-time and/or discrete time samples into numerical representations of those samples. Detector 110 may also include one or more digital filters (or other digital signal processing circuitry) following the ADC, such as for selectively emphasizing the desired heart depolarization information relative to other acquired signal content. Detector 110 also includes an output providing a periodically sampled data cardiac signal $x(n)$ to a cardiac signal processor module 112 of controller 114. Controller 114 is capable of sequencing through various control states such as, for example, by using a digital microprocessor having executable instructions stored in an associated instruction memory circuit, a microsequencer, or a state machine. In operation, by executing these instructions, controller 114 provides the functionality of cardiac signal processor module 112, as well as providing control signals to cardiac signal detector 110, depolarization detector 111, and an energy output circuit 116. In one example, cardiac signal processor module 112 includes a beat/noise discrimination module 118, which is further discussed below. Energy output circuit 116 provides pacing or resynchronization pulses, antitachyarrhythmia pacing (ATP) pulses, defibrillation shocks, lower energy cardioversion shocks, and/or other appropriate cardiac therapy to heart 104. Device 102 also includes a battery or other power source 120.

In the example of FIG. 1, device 102 includes a depolarization detector 111 that extracts a depolarization associated with a contraction (or "beat") of a chamber of heart 104 (such as, by way of example, but not by way of limitation, a depolarization associated with a ventricular heart contraction). In one example, depolarization detector 111 includes a level detector that declares a depolarization to have been detected if an amplitude of the intrinsic cardiac signal received from cardiac signal detector 110 exceeds a predetermined threshold value. Other criteria, devices, or techniques may be additionally or alternatively used by depolarization detector 111 to determine whether a depolarization is present on the intrinsic cardiac signal. Moreover, this determination can be made using either a continuous time representation derived from the intrinsic cardiac signal, or using a sampled data representation derived from the intrinsic cardiac signal (such as the sampled data cardiac signal x(n) provided by cardiac signal detector 110 to cardiac signal processor 112).

Figure 2:
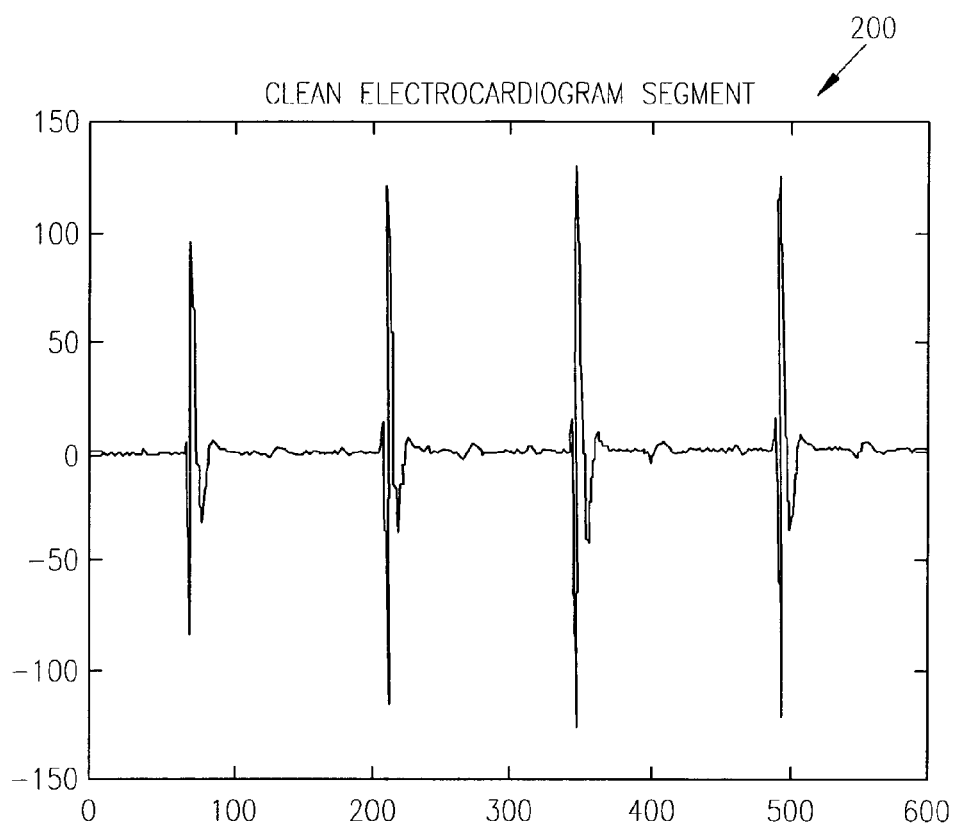
FIG. 2 is a graph illustrating generally a relatively noise-free cardiac signal.
Figure 3A:
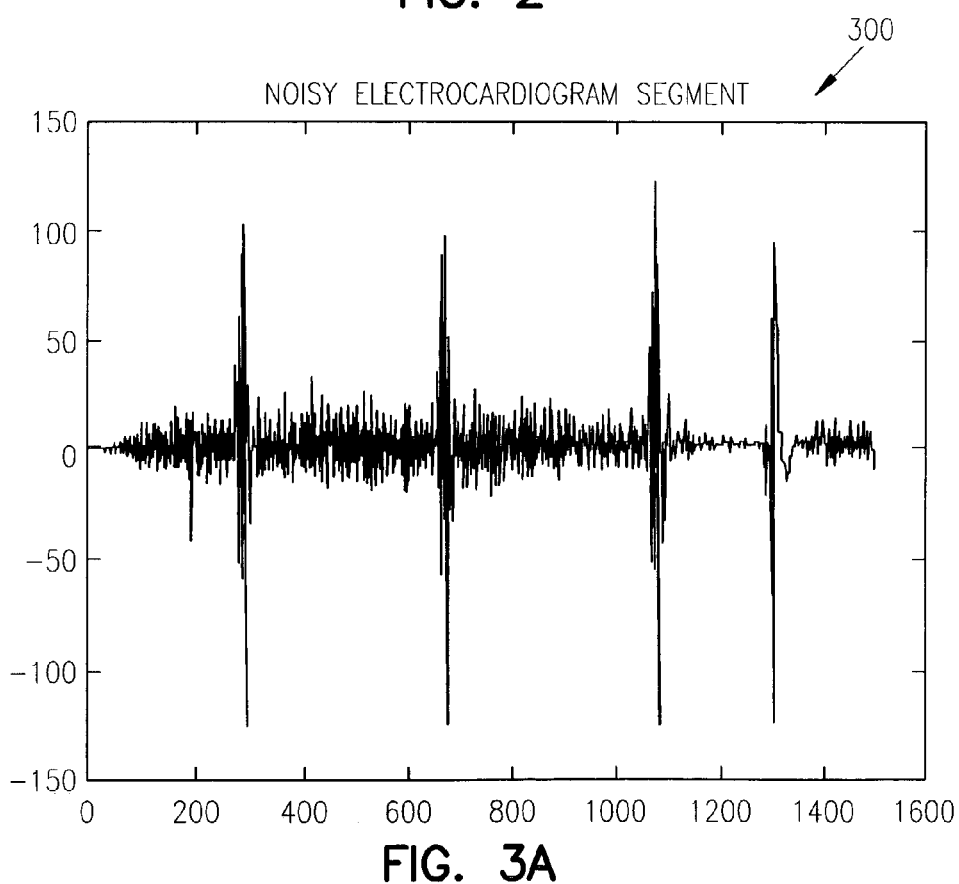
FIG. 3A is a graph illustrating generally a relatively noisy cardiac signal.
Figure 3B:
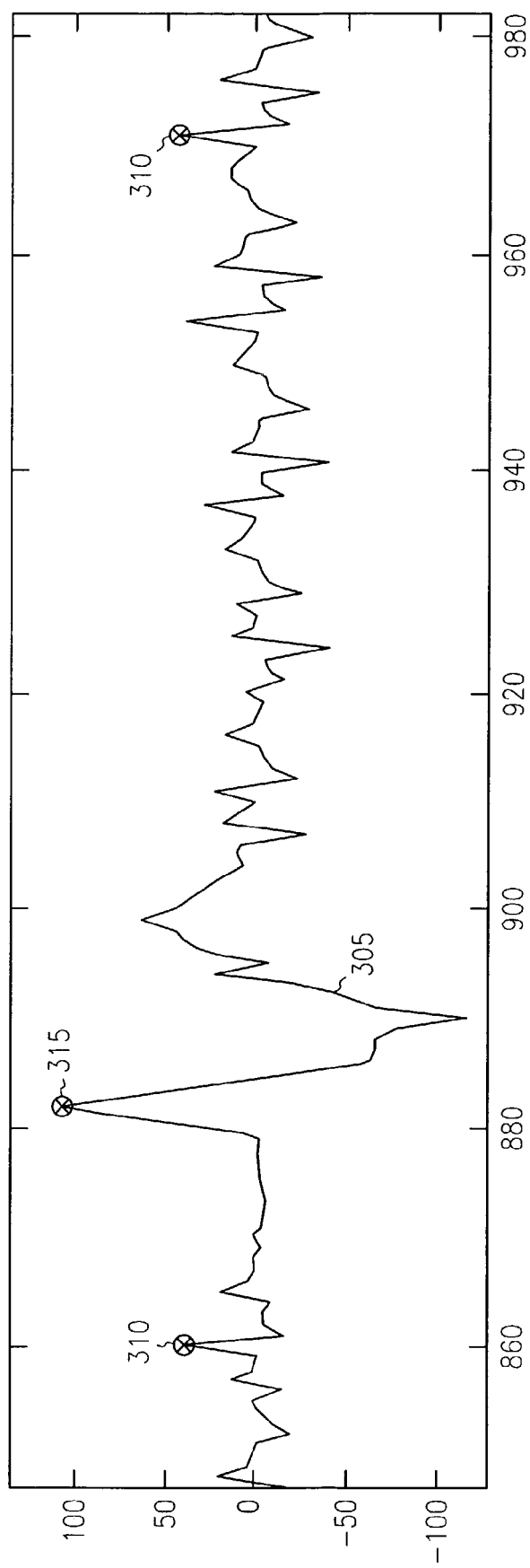
FIG. 3B is a graph illustrating in more detail a portion of a relatively noisy sampled cardiac signal.

FIG. 2 is a graph illustrating generally a relatively noise-free cardiac signal 200 obtained from electrodes associated with heart 104. FIG. 3A is a graph illustrating generally a relatively noisy cardiac signal 300 similarly obtained from electrodes associated with heart 104. In the example of FIG. 3A, the additional noise may make the underlying heart chamber depolarizations difficult to detect, since the noise may include frequencies within the passband of the depolarizations and may, therefore, erroneously be level-detected as an actual heart depolarization. FIG. 3B is a graph illustrating in more detail a portion of a relatively noisy sampled cardiac signal 305, which is similarly obtained from electrodes associated with heart 104. The example of FIG. 3B illustrates, among other things, noise peak amplitude samples 310 and a cardiac beat peak amplitude sample 315. As illustrated by the example of FIG. 3B, the morphology and slew rate about noise peak sample 310 is different from that about cardiac beat peak sample 315. As described below, such differences can be used to distinguish between a noise peak sample and a cardiac depolarization peak sample. This information, in turn, may be used to avoid the inappropriate withholding or delivery of therapy based on an erroneous detection of a noise peak sample as a cardiac beat.

In the example of FIG. 1, cardiac signal processor 112 includes a beat/noise discrimination module 118. Beat/noise discrimination module 118 includes an input, at node/bus 122, that receives the sampled cardiac signal x(n). Beat/noise discrimination module 118 also includes an output, at node/bus 124, providing a beat/noise indicator that provides a determination of whether an amplitude peak on the sampled cardiac signal x(n) represents a heart beat or is instead merely indicative of noise. In one example, the beat/noise discrimination determination is made using a weighted averager 126, which receives the sampled cardiac signal x(n) and computes a weighted average that is output at node/bus 128. In one example, the weighted average is a normalized weighted average (NWA). In one example, a normalized weighted average is computed according to Equation 1.

$$NWA=[P(n-1)+2*P(n)+P(n+1)]/[4*P(n)] \quad (1)$$

In Equation 1, P(n) represents a peak amplitude sample of the sampled cardiac signal x(n), P(n−1) represents the sample immediately preceding the peak amplitude sample P(n), and P(n+1) represents the sample immediately subsequent to the peak amplitude sample P(n). In one example, the peak amplitude sample P(n) is that peak amplitude sample corresponding to a peak amplitude of a depolarization detected by depolarization detector 111. In one example, in which the sampled cardiac signal x(n) is sampled at a 200 Hz sample rate, a 5 millisecond time interval separates the samples P(n) and P(n−1) and the samples P(n) and P(n+1). In another example, in which the sampled cardiac signal x(n) is sampled at a 256 Hz sample rate, about a 3.9 millisecond time interval separates the samples P(n) and P(n−1) and the samples P(n) and P(n+1). These examples are merely illustrative; other sample rates are also possible. Moreover, Equation 1 need not be limited to using the immediately preceding and subsequent samples, but could alternatively use other preceding and subsequent samples, such as illustrated by way of example, but not by way of limitation, in Equation 2.

$$NWA=[P(n-k)+2*P(n)+P(n+k)]/[4*P(n)] \quad (2)$$

In Equation 2, $k \geq 2$ can be used, such as, for example, at higher sampling rates (for example, sampling rates greater than or equal to 512 kHz). In one example, the samples preceding and subsequent to peak sample, P(n), are selected to fall within the time period of the corresponding depolarization complex to be distinguished from noise. For example, a QRS depolarization complex of a ventricular contraction typically exhibits a corresponding cardiac signal deviation away from baseline that lasts between 80 milliseconds and 120 milliseconds. For P(n), P(n−1), and P(n+1) to fall within a 120 millisecond QRS depolarization, the time difference between the peak sample and the preceding sample should be less than about 60 milliseconds; similarly, the time difference between the peak sample and the subsequent sample should be less than about 60 milliseconds. For P(n), P(n−1), and P(n+1) to fall within an 80 millisecond QRS depolarization, the time difference between the peak sample and the preceding sample should be less than about 40 milliseconds; similarly, the time difference between the peak sample and the subsequent sample should be less than about 40 milliseconds. These examples are offered for illustrative purposes, and are not intended to be limiting.

In the above example, as illustrated by Equations 1 and 2, the weighted averages are normalized. For example, in one embodiment, cardiac signal detector 110 includes an automatic gain control (AGC) circuit, which adjusts the amplitude of the detected depolarizations to make better use of the available dynamic range of the signal processing circuits. In such an example, normalization of the weighted average to the peak value of the depolarization complex may be desirable to eliminate the effect of the AGC in computing the weighted average. In another example, in which cardiac signal detector 110 does not include such an AGC, no normalization to the peak value of the depolarization complex need be used. In a non-normalized example, the term P(n) is removed from the denominator of Equations 1 and 2 to compute a non-normalized weighted average.

Figure 4:
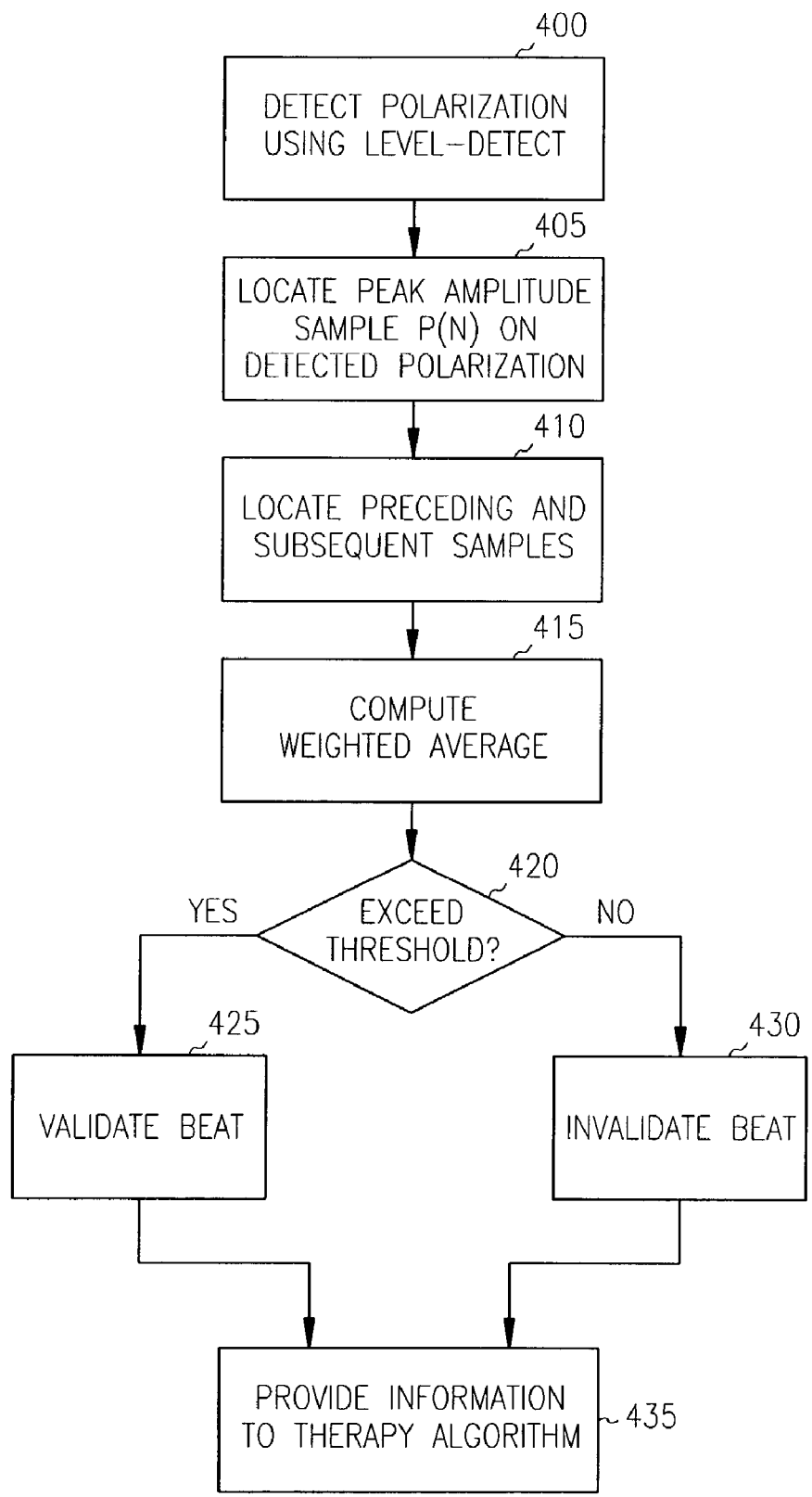
FIG. 4 is a flow chart illustrating generally, by way of example, but not by way of limitation, using a weighted average to validate or invalidate a depolarization detected by level-detecting or other techniques.
Figure 5:
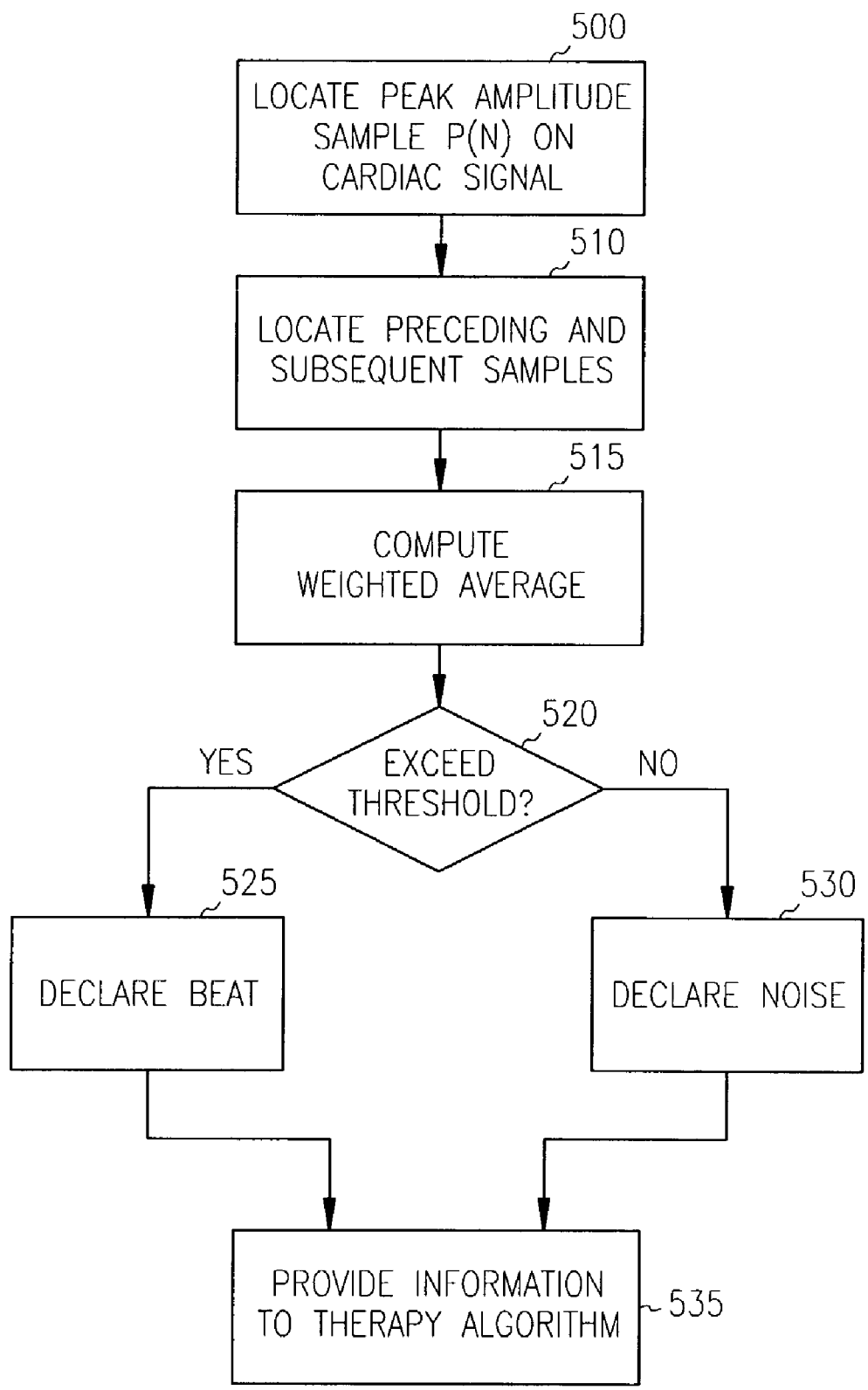
FIG. 5 is a flow chart illustrating generally, by way of example, but not by way of limitation, using a weighted average to detect a depolarization.

In the example of FIG. 1, beat/noise discrimination module also includes a hardware, software, or firmware comparator 130 that compares the computed NWA to a predetermined noise threshold 132. If the computed NWA exceeds the noise threshold 132, then the peak sample is deemed a beat; otherwise it is deemed to be noise. An indication of whether the peak sample is a beat or noise is output at node/bus 124. In one example, controller 114 provides one or more cardiac rhythm management therapy control signals that trigger therapy delivery by energy output circuit 116. Controller 114 includes one or more algorithms that determine whether therapy is needed using heart rhythm information that is based on detected depolarizations. The level-detecting or other techniques used by depolarization detector 111 to detect a heart depolarization may be susceptible to myopotential or other noise that may inappropriately inhibit, or inappropriately trigger, therapy delivery. Beat/noise discrimination module 118 provides at least one additional criteria to validate (or invalidate, i.e., deem as noise) a depolarization detected by depolarization detector 111. Alternatively, beat/noise discrimination module 118 may replace depolarization detector 111 to detect a depolarization rather than validating or invalidating an already-detected depolarization. FIGS. 4 and 5 illustrate examples of these different operating modes.

FIG. 4 is a flow chart illustrating generally, by way of example, but not by way of limitation, using a weighted average to validate or invalidate a depolarization detected by level-detecting or other techniques. In the example of FIG. 4, at 400, a depolarization is detected, such as by depolarization detector 111 using level detecting and/or other techniques. At 405, a peak amplitude sample P(n) is located at the peak amplitude of the detected depolarization. At 410, an immediately preceding sample P(n−1) and an immediately subsequent sample P(n+1) are located. At 415, a weighted average is computed, such as described in the examples of Equations 1 or 2. At 420, if the weighted average exceeds a predetermined threshold, the depolarization detected at 400 is validated at 425 as an actual beat; otherwise the depolarization detected at 400 is invalidated at 430, i.e., deemed noise. At 435, an indication of whether the depolarization detected at 400 was validated or invalidated is provided to a therapy algorithm used by controller 114, such as for determining whether the heart rhythm indicates that responsive therapy should be delivered by device 102.

FIG. 5 is a flow chart illustrating generally, by way of example, but not by way of limitation, using a weighted average to detect a depolarization. In the example of FIG. 5, at 500, a peak amplitude sample P(n) is located on the sampled cardiac signal x(n), such as by using a digital peak detector. At 510, an immediately preceding sample P(n−1) and an immediately subsequent sample P(n+1) are located. At 515, a weighted average is computed, such as described in the example of Equations 1 or 2. At 520, if the weighted average exceeds a predetermined threshold, a detected depolarization is declared at 525; otherwise the peak amplitude sample is declared noise at 530. At 535, an indication of whether a depolarization was detected and declared at 525 is provided to a therapy algorithm used by controller 114, such as for determining whether the heart rhythm indicates that responsive therapy should be delivered by device 102.

Figure 6:
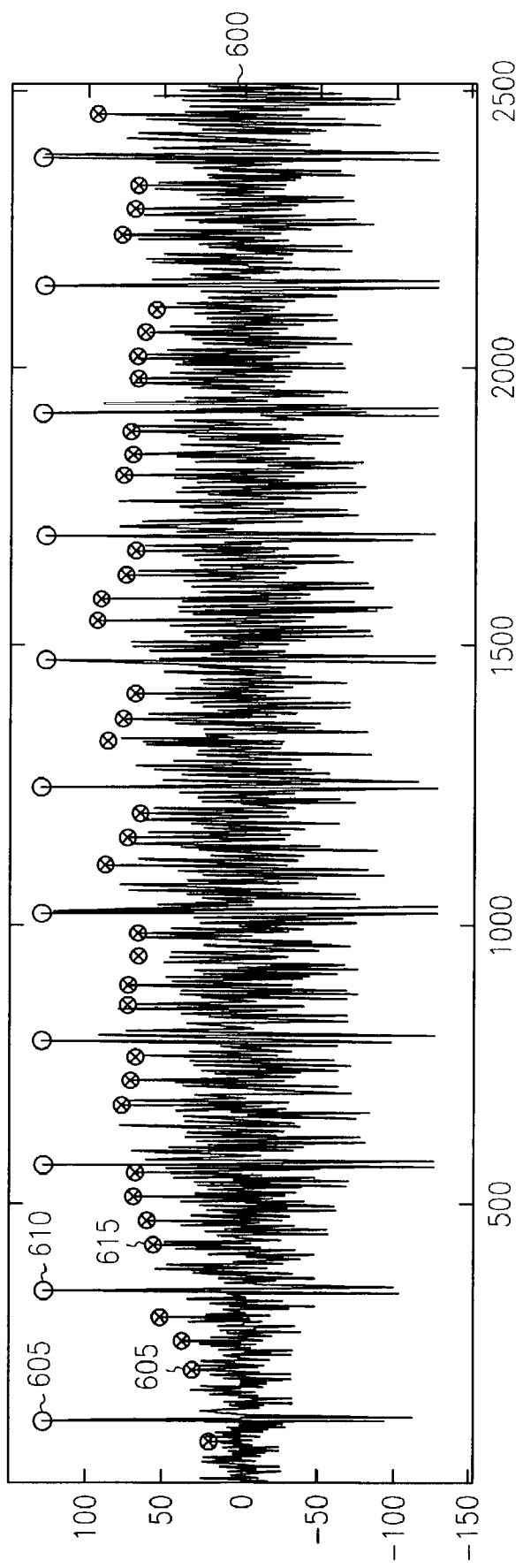
FIG. 6 is a graph illustrating generally, by way of example, but not by way of limitation, experimental data in which detected depolarizations were validated using the technique described in the flow chart of FIG. 4.

FIG. 6 is a graph illustrating generally, by way of example, but not by way of limitation, experimental data in which detected depolarizations were validated using the technique described in the flow chart of FIG. 4. In the example of FIG. 6, heart signal 600 was obtained from (1) right ventricular apical tip and (2) right ventricular shock coil electrodes associated with a subject's heart 104. The amplitude peaks of heart signal 600 that are marked by circles (such as 605) represent level-detected depolarizations. The level-detected depolarizations marked by open circles (such as 610) were validated as actual cardiac beats. The level-detected depolarizations that are marked by circles having X's (such as 615) were invalidated as actual cardiac beats, i.e., deemed noise. In this example, a predetermined noise threshold 132 value of 0.62 was used. The average value of NWA for actual beats was 0.89, with a standard deviation of 0.08. The average value of NWA for noise peaks was 0.43, with a standard deviation of 0.08.

In a further example, a refractory period is used in conjunction with the validation technique illustrated in FIG. 4. In this example, any beat that is validated at 425 is followed by a refractory period of predetermined duration (e.g., between about 40 milliseconds and about 80 milliseconds). During the refractory period, all observed peak amplitude signals are deemed noise. Only after the refractory period expires are subsequent amplitude peaks validated or invalidated using the weighted average techniques described in this document.

Figure 7:
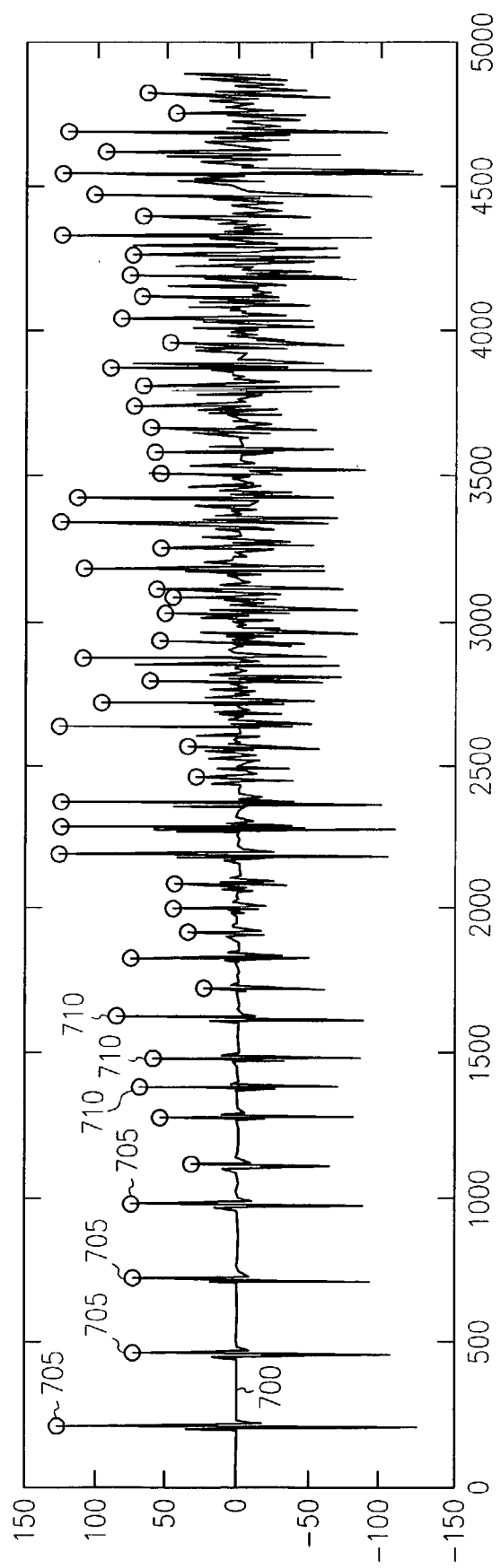
FIG. 7 is a graph illustrating generally, by way of example, but not by way of limitation, experimental data in which detected depolarizations (during the onset of ventricular fibrillation) were validated using the technique described in the flow chart of FIG. 4.

FIG. 7 is a graph illustrating generally, by way of example, but not by way of limitation, experimental data in which detected depolarizations (during the onset of an arrhythmia, such as ventricular fibrillation) were validated using the technique described in the flow chart of FIG. 4. Unlike the example of FIG. 6, for which depolarizations were validating during normal sinus rhythm (NSR), in FIG. 7, depolarizations were validated during the onset of a ventricular fibrillation (VF) episode. The morphologies (shapes) of NSR cardiac complexes may differ substantially from those of VF cardiac complexes. However, as illustrated by FIG. 7, the technique described in the flow chart of FIG. 4 is also effective at distinguishing cardiac complexes from noise even when such cardiac complexes are VF complexes instead of NSR complexes. In FIG. 7, the circles 705 represent level-detected cardiac depolarizations that were validated as actual cardiac beats during normal sinus rhythm. The circles 710 (e.g., the seventh and all subsequent beats illustrated in FIG. 7) represent level-detected cardiac depolarizations that were validated as actual cardiac beats during ventricular fibrillation, despite significant fluctuations in the cardiac signal due to the ventricular fibrillation. Heart signal 700 represents a period of time before and during the onset of a VF episode. Heart signal 700 was obtained from (1) right ventricular apical tip and (2) right ventricular shock coil electrodes associated with a subject's heart 104. In this example, a predetermined noise threshold 132 value of 0.62 was used.

It is to be understood that the above description is intended to be illustrative, and not restrictive. For example, the above-discussed examples may be used in combination with each other. Many other embodiments will be apparent to those of skill in the art upon reviewing the above description. The scope of the invention should, therefore, be determined with reference to the appended claims, along with the full scope of equivalents to which such claims are entitled. Moreover, in the following claims, the terms "first," "second," "third," etc. are used merely as labels, and are not intended to impose numeric requirements on their objects.

What is claimed is:

1. A system comprising:
   a cardiac signal detector, comprising a detector input configured to be coupled to a first electrode associated with a heart, and comprising a detector output providing a sampled cardiac signal; and
   a signal processor circuit, coupled to the detector output, the signal processor circuit configured to distinguish, using a peak sample, a preceding sample to the peak sample, and a subsequent sample to the peak sample, a cardiac depolarization from noise, and in which the signal processor circuit is configured to form an average statistic computed using as data points an amplitude of the peak sample from a baseline, an amplitude of the preceding sample from the same baseline, and an amplitude of the subsequent sample from the same baseline, and to distinguish between a cardiac depolarization and noise by comparing the statistic to a predetermined threshold value.

2. The system of claim 1, in which the signal processor circuit is configured to compute a weighted average using the peak sample, the preceding sample, and the subsequent sample, and to distinguish between a cardiac depolarization and noise by comparing the weighted average to a predetermined threshold value.

3. The system of claim 2, in which the signal processor circuit is configured to compute a normalized weighted average using the peak sample, the preceding sample, and the subsequent sample, and to distinguish between a cardiac depolarization and noise by comparing the normalized weighted average to a predetermined threshold value.

4. The system of claim 3, in which the normalized weighted average is computed as NWA=[P(n−1)+2*P(n)+P(n+1)]/[4*P(n)].

5. The system of claim 4, in which the predetermined threshold value is about 0.62.

6. The system of claim 1, further comprising an electrode coupled to the detector input.

7. The system of claim 6, further comprising an intracardiac leadwire carrying the electrode.

8. The system of claim 1, further comprising:
an implantable device including the cardiac signal detector and the signal processing circuit; and
a remote user interface, configured to be communicatively coupled to the implantable device.

9. The system of claim 1, in which the signal processor circuit is configured to distinguish a normal sinus rhythm cardiac depolarization from noise.

10. The system of claim 1, in which the signal processor circuit is configured to distinguish an arrhythmic cardiac depolarization from noise.

11. The system of claim 10, in which the signal processor circuit is configured to distinguish a ventricular fibrillation cardiac depolarization from noise.

12. An implantable cardiac rhythm management device comprising:
a cardiac signal detector, comprising a cardiac signal detector input configured to be coupled to a first electrode associated with a heart to receive an intrinsic cardiac signal therefrom, and comprising a cardiac signal detector output providing a sampled cardiac signal; and
a depolarization detector circuit, coupled to the first electrode, the depolarization detector circuit including a level detector circuit configured to detect an intrinsic heart depolarization on the intrinsic cardiac signal; and
a signal processor circuit, coupled to the cardiac signal detector output and the depolarization detector circuit, the signal processor circuit configured to validate the intrinsic heart depolarization detected by the depolarization detector circuit by distinguishing a cardiac depolarization from noise, using an average statistic computed using as data points an amplitude, from a baseline, of a peak sample of the sampled cardiac signal, an amplitude, from the same baseline, of a preceding sample to the peak sample of the sampled cardiac signal, and an amplitude, from the same baseline, of a subsequent sample to the peak sample of the sampled cardiac signal, wherein the peak sample of the sampled cardiac signal is associated with a peak of the intrinsic heart depolarization detected by the depolarization detector circuit.

13. The device of claim 12, in which the signal processor circuit is configured to compute a weighted average using the peak sample, the preceding sample, and the subsequent sample, and to distinguish between a cardiac depolarization and noise by comparing the weighted average to a predetermined threshold value.

14. The system of claim 13, in which the weighted average is computed as NWA=[P(n−1)+2*P(n)+P(n+1)]/[4*P(n)].

15. The system of claim 12, in which the signal processor circuit is configured to distinguish a normal sinus rhythm cardiac depolarization from noise.

16. The system of claim 12, in which the signal processor circuit is configured to distinguish an arrhythmic cardiac depolarization from noise.

17. The system of claim 12, in which the signal processor circuit is configured to distinguish a ventricular fibrillation cardiac depolarization from noise.

18. A method comprising:
sampling a cardiac signal;
detecting a peak sample from the cardiac signal;
detecting a preceding sample to the peak sample from the cardiac signal;
detecting a subsequent sample to the peak sample from the cardiac signal;
distinguishing, using the peak sample, the preceding sample, and the subsequent sample, a cardiac depolarization from noise, in which the distinguishing comprises:
computing an average statistic, the statistic computed using as data points an amplitude of the peak sample from a baseline, an amplitude of the preceding sample from the same baseline, and an amplitude of the subsequent sample from the same baseline; and
distinguishing between a cardiac depolarization and noise by comparing the statistic to a predetermined threshold value.

19. The method of claim 18, in which the computing comprises:
computing a weighted average using the peak sample, the preceding sample, and the subsequent sample; and
distinguishing between a cardiac depolarization and noise by comparing the weighted average to a predetermined threshold value.

20. The method of claim 19, in which the computing comprises:
computing a normalized weighted average using the peak sample, the preceding sample, and the subsequent sample; and
distinguishing between a cardiac depolarization and noise by comparing the normalized weighted average to a predetermined threshold value.

21. The method of claim 20, in which the computing the normalized weighted average is computed as NWA=[P(n−1)+2*P(n)+P(n+1)]/[4*P(n)].

22. The method of claim 21, in which the comparing the normalized weighted average to the predetermined threshold value comprises using a predetermined threshold value of about 0.62.

23. The method of claim 18, further comprising programming the predetermined threshold value.

24. The method of claim 18, further comprising detecting the cardiac signal using an electrode.

25. The method of claim 24, further comprising intravascularly disposing the electrode within the heart.

26. The method of claim 18, further comprising communicating an indication of whether a peak sample is a depolarization or noise to a remote location.

27. The method of claim 18, in which the distinguishing a cardiac depolarization from noise comprises distinguishing a normal sinus rhythm cardiac depolarization from noise.

28. The method of claim 18, in which the distinguishing a cardiac depolarization from noise comprises distinguishing an arrhythmic cardiac depolarization from noise.

29. The method of claim 18, in which the distinguishing a cardiac depolarization from noise comprises distinguishing a ventricular fibrillation cardiac depolarization from noise.

30. A method comprising:

detecting an intrinsic cardiac signal;

detecting a depolarization on the intrinsic cardiac signal by comparing a level of the intrinsic cardiac signal to a level threshold value to yield a level-detected depolarization;

sampling the intrinsic cardiac signal to produce a sampled cardiac signal;

detecting a peak sample from the sampled cardiac signal, wherein the peak sample is associated with the level-detected depolarization;

detecting a preceding sample to the peak sample from the sampled cardiac signal;

detecting a subsequent sample to the peak sample from the sampled cardiac signal; and validating, using the peak sample, the preceding sample, and the subsequent sample, the level-detected depolarization by computing a weighted average using the peak sample, the preceding sample, and the subsequent sample, and comparing the weighted average to a noise threshold.

31. The method of claim 30, in which the computing the weighted average is computed as $NWA=[P(n-1)+2*P(n)+P(n+1)]/[4*P(n)]$.

32. The method of claim 30, in which the validating comprises validating a normal sinus rhythm cardiac depolarization.

33. The method of claim 30, in which the validating comprises validating an arrhythmic cardiac depolarization from noise.

34. The method of claim 30, in which the validating comprises validating a ventricular fibrillation cardiac depolarization from noise.

35. A system comprising:

a cardiac signal detector, comprising a detector input configured to be coupled to a first electrode associated with a heart, and comprising a detector output providing a sampled cardiac signal; and a signal processor circuit, coupled to the detector output, the signal processor circuit configured to distinguish a cardiac depolarization from noise, the distinguishing using an amplitude of a peak sample from a baseline, an amplitude, from the same baseline, of a preceding sample to the peak sample, and an amplitude, from the same baseline, of a subsequent sample to the peak sample, and in which the signal processor circuit is configured to form a an average of each of the amplitudes of the peak sample, the preceding sample, and the subsequent sample, and to distinguish between a cardiac depolarization and noise by comparing the average to a predetermined threshold value.

* * * * *

UNITED STATES PATENT AND TRADEMARK OFFICE
CERTIFICATE OF CORRECTION

PATENT NO.        : 7,215,993 B2                                        Page 1 of 1
APPLICATION NO.   : 10/213364
DATED             : May 8, 2007
INVENTOR(S)       : Lin It is certified that error appears in the above-identified patent and that said Letters Patent is hereby corrected as shown below:

In column 14, line 22, in Claim 35, after "form" delete "a".

Signed and Sealed this

Tenth Day of July, 2007

JON W. DUDAS
*Director of the United States Patent and Trademark Office*